United States Patent [19]

Rotello

[11] 3,963,022

[45] June 15, 1976

[54] COMFORT ATHLETIC SUPPORTER

[76] Inventor: Joseph Vincent Rotello, 6052 Welch St., Arvada, Colo. 80004

[22] Filed: Sept. 5, 1975

[21] Appl. No.: 610,543

[52] U.S. Cl. .................................. 128/158; 2/403
[51] Int. Cl.$^2$ ............................................ A61F 5/40
[58] Field of Search ............... 2/224 A, 224 R, 225, 2/226, 67; 128/157, 158, 159, 160, 161, 162

[56] References Cited
UNITED STATES PATENTS

| 722,121 | 3/1903 | Lupfer | 128/161 |
| 775,288 | 11/1904 | Riley | 128/161 |
| 1,230,451 | 6/1917 | Walsky | 128/158 X |
| 1,294,709 | 2/1919 | Rohwer | 128/158 |
| 2,056,773 | 10/1936 | Dann | 2/224 A |

Primary Examiner—H. Hampton Hunter

[57] ABSTRACT

The present invention relates to an athletic supporter which comprises a single fabric panel and a single piece elastic waistband, the fabric panel being of sufficient length to extend from the lower front abdomen of the wearer, between the wearer's legs, and terminate at the mid-posterior area of the wearer. The single piece elastic waistband attaches to the fabric piece and loops around the wearer's waist, passing through a passageway at the first end of the fabric panel, upon which the fabric panel gathers causing a bulging which forms a support cup of the athletic supporter.

10 Claims, 4 Drawing Figures

COMFORT ATHLETIC SUPPORTER

BACKGROUND OF THE INVENTION

1. Field of Invention

The present invention relates to the field of athletic supporters worn by men and boys in participating in athletic activities. The typical athletic supporter presently available consists of a panel of material which terminates between the wearer's legs, at which point support straps are attached. The attachement of support straps at the point creates a bulkiness between the wearer's legs which is a source of possible irritation and annoyance. Additionally, in order to form the panel of material into the desired cup, a seam is required in the area of the wearer's scrotum, which is also a source of irritation and annoyance. Further, the material required to provide adequate support in an athletic support of this kind is a heavy duty elasticised material which can also be the source of irritation and annoyance.

Other styles of supporters available on the market include support briefs, which cover more area of the wearer's torso then is necessary and which can cause irritation as a result of binding in the crotch and around the wearer's legs.

2. Prior Art

There has been little done recently with regard to differing designs for athletic supporters. In a related area, that of regular undergarments, there has been developed an undergarment which consists of a single piece of fabric extending from the waist of the wearer in front, between the wearer's legs and to his waist in the rear with an elastic waistband connecting the two. However, this garment suffers from many defects which have been corrected by the present invention and which will be discussed in detail later.

SUMMARY OF THE INVENTION

The purpose of the present invention is to provide a simply constructed comfortable and effective athletic supporter for wear while participating in athletic activities, both strenuous and nonstrenuous. The garment, as a result of its construction, fits comfortably and effectively to the wearer's body and provides proper support without irritation or annoyance. The garment is so constructed that the single piece elastic waistband seeks its own proper position on the wearer's body for maximum comfort. The single piece waistband provides maximum adjustability to accommodate both long and short torsos as well as broad and thin torsos. The construction of the garment is such that the upper front of the fabric panel gathers along the waist band creating the support cup. Depending on the size and shape of the wearer, the gathering will adjust to the wearer's torso, thereby creating the proper size and shaped cup.

OBJECTS OF THE INVENTION

An object of the present invention is to provide a comfortable and effective athletic supporter.

A further object of the invention is to provide an athletic supporter which adjusts easily and fits a variety of sizes and shapes of torsos.

DETAILED DESCRIPTION OF THE DRAWINGS

Figure 1:
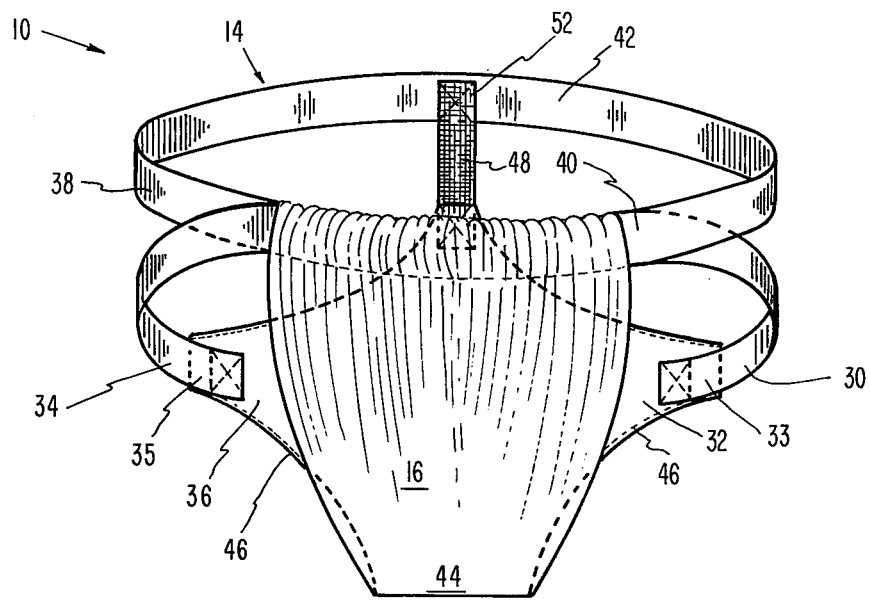
FIG. 1 discloses a front, perspective view of the present invention.
Figure 2:
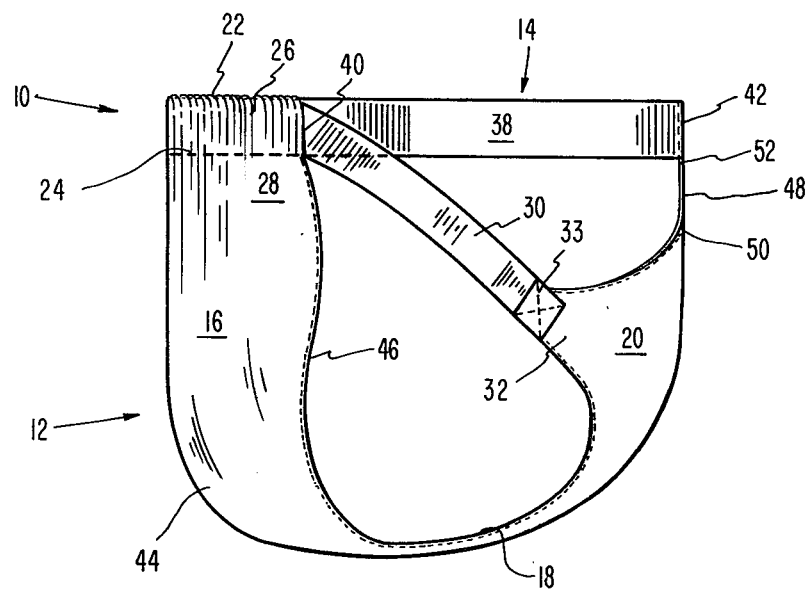
FIG. 2 discloses a side planar view of the present invention.
Figure 3:
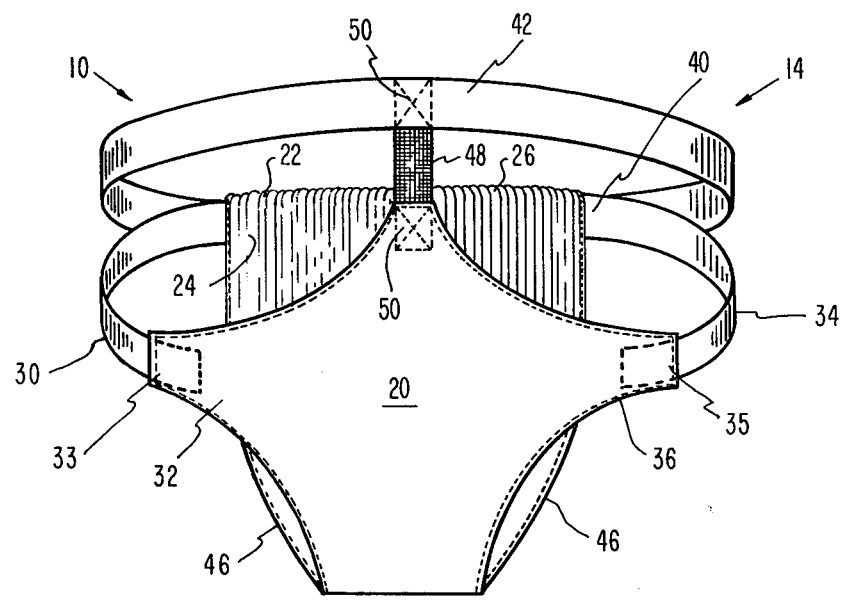
FIG. 3 discloses a rear, perspective view of the present invention.

Reference is made to FIGS. 1-3 of the drawings, which figures will be referred to as a group. In those figures as shown a comfort athletic supporter 10 comprising a single fabric panel 12 and a single piece elastic waistband 14. The single fabric panel comprises a first end 16, a central portion 18, and a second end 20. The single fabric panel 12 is of sufficient length to extend from the lower front abdominal region of the wearer, between the wearer's legs, and terminate at the mid-posterior area of the wearer.

Figure 4:
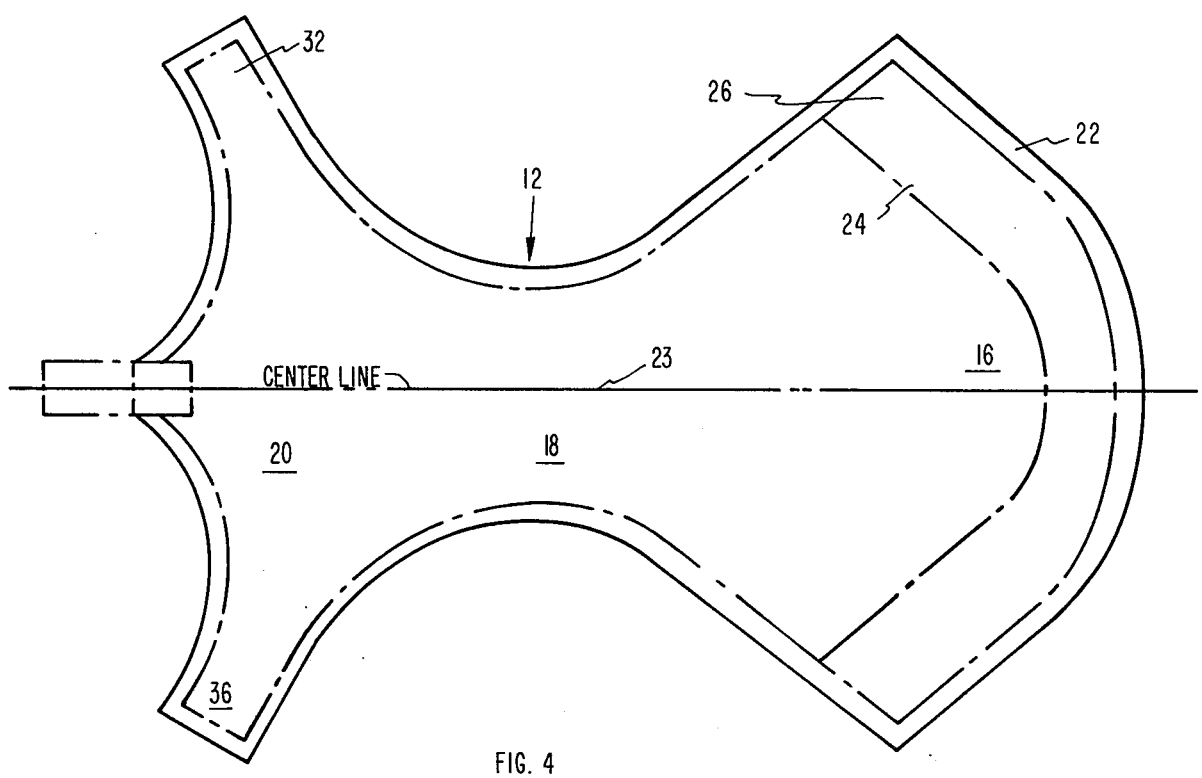
FIG. 4 discloses a lay-out view of a part of the present invention.

The shape of the fabric panel, as more specifically shown in FIG. 4, includes sufficient length at the first end 16 to fully cover the width of the wearer's abdominal region, a narrowing at the central portion 18 to provide a part of the panel to comfortably fit between the wearer's legs, and a fan shaped configuration at the second end 20, the purpose for which will be described in more detail later. The first end 16 of the fabric panel 12 includes a boundary 22 generally transverse to a lateral center line 23 of the fabric panel 12, as shown in FIG. 4.

The boundary 22 is curvilinear in shape, the purpose for which will be described in detail later. Approximately parallel to the boundary 22 is a hem 24 which is constructed in such a way as to provide a passageway 26 between the boundary 22 and the hem 24, and between double layers of fabric created by the formation of the hem 24, the purpose for which will also be described later in detail.

The single piece elastic waistband is attached to the fabric panel and loops around the wearer's torso approximately at the waist. The waistband 14 comprises a first end 30 which is secured to a first side 32 of the fan shaped second end 20 of the fabric panel. The first end 30 of the waistband 14 is secured to the first side 32 at 33, by sewing or any other similar related method such as snapping or buckling. A second end 34 of the waistband 14 is secured to a second side 36 of the fan shaped second end 20 of the panel case 12, by sewing or some other similar method such as snapping or buckling as shown at 35. As is evident from any of FIGS. 1-3, the elastic waistband 14 also partially includes the legs of the wearer.

A central section 38 of the elastic waistband 14 loops around the torso in such a way that portions of the central section 38 cross in front of the wearer's torso to form a double thickness, as shown at 40, and pass through the passageway 26 created in the fabric panel 12 by the hem 24 as a double thickness. A middle portion of the central section 38 of the waistband 14 passes around the back of the wearer, as shown at 42 in a single thickness.

By securing the two ends 30 and 34 of the waistband 14 to the back portion of the fabric panel 12, and allowing the central portion 38 of the waistband 14 to loop around the front of the wearer, pass through the passageway 26 and around the back of the wearer, the garment as a whole can adjust to the particular size and shape of an individual wearer. If the wearer should happen to be tall and slim, then that portion of the waistband 14 surrounding the wearer's waist would be shorter, allowing more of the waistband to extend from the passageway 26 to the connections on either side at 33 and 35 with the back portion 20 of the fabric panel 12, thereby providing more leg room for the taller wearer. On the contrary, if the wearer is short and stocky, more of the waistband is available for use surrounding the wearer and less is needed to provide leg room.

As a result of the curvilinear shape of boundary 22, and the passageway 26 which is essentially parallel to the boundary 22, and the fact that the waistband 14 passes through the passageway 26, the front portion 16 of the fabric panel 12 is forced to gather along the waistband 14 as shown at 28. This gathering of the fabric panel 12 causes a bulging of the front portion 16 of the fabric panel 12 as shown at 44 to form a supporting cup for the support of the wearer's genitals. The gathering 28 of the front portion 16 of the fabric panel 12 along the waistband 14 does not cause discomfort to the wearer for the reason that the waistband 14, because of the adjustability previously discussed, seeks to position itself at the natural indentation of the human torso which occurs at the base of the abdominal muscles just below the waist of the wearer. Consequently, without regard to the stature of the individual wearer, and therefore the amount of gathering required, the garment remains comfortable for the wearer in the area of the waistband as it passes around the front abdominal region of the wearer. The front portion 16 of the fabric panel may be spread to almost its full width with very little gathering in the case of a large or heavy set torso, may be gathered extensively and thereby narrowed considerably in the case of a thin or smaller torso, or may seek some position in between those extremes, depending upon the actual size and shape of the torso of the wearer in question.

The sides of the fabric panel 12 which are generally aligned with the lateral center line 23 contain a hem 46, having essentially no elasticity. The essentially non-elastic hem 46 cooperates with the gathering 28 to properly form the support cup desired by the garment in question. The essentially non-elastic hem 46 further provides for a proper fit of the garment as it passes between the wearer's legs at 18, by maintaining a firm fabric line with no uncomfortable gathering of the edges of the fabric panel 12 as it passes between the wearer's legs. Another effect of the presence of the essentially non-elastic hem 46 is to insure the presence of material from the garment existing between the wearer's scrotum and his legs to avoid irritation to the wearer's skin as a result of rubbing and abrasion that might occur from the strenuous athletic activities. The essentially non-elastic hem 46 continues around to the second end 20 of the fabric panel 12 in the mid-posterior area of the wearer to maintain the fan shaped second end 20 in its proper position for maximum comfort to the wearer.

An additional element of the garment of the present invention includes a vertically aligned essentially non-elastic strap 48 which secures the fan shaped second end 20 of the fabric panel 12 to the back portion 42 of the elastic waistband 14 by sewing or some similar means of attachment, such as snapping or buckling, as shown at 50 and 52. The purpose of strap 48 is to maintain the proper position and alignment between the fan shaped second end 20 of the fabric panel 12 and the central portion 38 of the waistband 14. A possible means of attachment of the strap 48 to either the second end 20 or the waistband 14 by an adjustable attachment, such as Velcro or the like to provide for adjustment of the strap 48.

The present invention contemplates the fabric panel 12 being constructed from a knitted cotton material in order to provide the proper limited elasticity in all directions. However, it is within the contemplation of the present invention that other materials may also be used, such as for example, cotton-synthetic blends, woven materials in a twill or broken point twill, elasticised material or any other variety of materials which would provide limited elasticity in all directions.

What is claimed is:
1. An athletic supporter for wear by males in strenuous and non-strenuous athletic activities comprising:
  a. a single fabric panel conforming to the lower human torso and of sufficient length to extend from a lower front abdominal region of the wearer, pass between the wearer's legs and terminate at a mid-posterior area of the wearer;
  b. the single fabric panel being shaped with sufficient width at a first end of the fabric piece to substantially cover the lower front abdominal region of the wearer, with sufficient narrowing at a central portion of the fabric panel to fit between the wearer's legs with comfort, and with a fan shaped configuration at a second end of the fabric panel terminating at the mid-posterior area of the wearer; and
  c. a single piece elastic waistband having a first end and a second end, the first end being attached to a first side of the fan shaped configuration of the fabric panel and the second end being attached to a second side of the fan shaped configuration of the fabric panel, and a central portion completely encircling the torso of the wearer in the area of the wearer's waist with a single layer of waistband in the area of the wearer's back and a double layer of waistband in the area of the wearer's abdomen, said first end of said fabric panel being loosely secured to said double layer of waistband over the abdomen.

2. An athletic supporter as claimed in claim 1 wherein:
  a. the first end of the fabric panel includes a boundary generally transverse to a lateral center line of the fabric panel, which boundary is curvilinear; and
  b. the curvilinear boundary includes a hem, which hem is secured to the fabric panel so as to provide at least double layers of fabric in the area of the curvilinear boundary and to create a passageway between the at least double layers of fabric generally parallel to the curvilinear boundary.

3. An athletic supporter as claimed in claim 2 wherein said securement comprises:
  a. the central portion of the elastic waistband encircling the wearer's torso in the area of the wearer's lower abdomen passes freely through the passageway created by the hem generally parallel to the curvilinear boundary of the fabric panel.

4. An athletic supporter as claimed in claim 3 wherein:
  a. the curvilinear boundary of the fabric panel gathers along the elastic waistband as the waistband encompasses the lower abdomen of the wearer to cause a bulging of the fabric panel in the lower frontal area of the wearer's torso to form a supporting cup for the wearer's genitals.

5. An athletic supporter as claimed in claim 4 wherein:
   a. the elastic waistband rests in a natural depression in the wearer's abdomen existing at the base of the wearer's abdominal muscles; and
   b. the curvilinear boundary of the fabric panel gathered along the elastic waistband widens and narrows along the elastic waistband to adjust to the size and shape of the torso of the wearer.

6. An athletic supporter as claimed in claim 4 wherein:
   a. the supporting cup is free of seams in the area of the wearer's genitals; and
   b. the supporting cup is free of gathered material between the wearer's legs.

7. An athletic supporter as claimed in claim 4 wherein:
   a. the peripheral areas of the fabric panel generally parallel to the lateral center line of the fabric panel are bounded by an essentially non-elastic hem; and
   b. the essentially non-elastic hem prevents gathering of the central portion of the fabric panel as the fabric panel fits between the wearer's legs.

8. An athletic supporter as claimed in claim 1 wherein:
   a. the fan shaped configuration of the fabric panel is secured to the elastic waistband in the area of the wearer's back by a vertically aligned, essentially non-elastic strap.

9. An athletic supporter as claimed in claim 1 wherein:
   a. the fabric panel comprises knit material.

10. An athletic supporter as claimed in claim 9 wherein:
    a. the knit material of the fabric panel comprises cotton.

* * * * *